(12) United States Patent
Compton et al.

(10) Patent No.: US 6,346,236 B1
(45) Date of Patent: Feb. 12, 2002

(54) SUNSCREENS FROM VEGETABLE OIL AND PLANT PHENOLS

(75) Inventors: David L. Compton; Joseph A. Laszlo, both of Peoria, IL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/535,826

(22) Filed: Mar. 28, 2000

(51) Int. Cl.[7] .................................................. A61K 7/44
(52) U.S. Cl. ........................................... 424/60; 560/55
(58) Field of Search ................................ 560/55; 424/60

(56) References Cited

U.S. PATENT DOCUMENTS

| | | | | |
|---|---|---|---|---|
| 5,426,210 A | * | 6/1995 | Kato et al. | 560/55 |
| 5,747,434 A | * | 5/1998 | Lamsa et al. | 508/485 |
| 5,824,326 A | * | 10/1998 | Crotty et al. | 424/401 |
| 5,908,615 A | * | 6/1999 | Taniguchi et al. | 424/60 |

FOREIGN PATENT DOCUMENTS

| | | | | |
|---|---|---|---|---|
| JP | 6-157272 | * | 6/1994 | 424/60 |

OTHER PUBLICATIONS

Artamonov et al, Chemical Abstacts, vol. 128, No. 257, 215b, 1998.*

Shimomura et al, Chemical Abstract, vol. 111, No. 180537x, 1989.*

Mayata et al, Chemical Abstracts, vol. 121, No. 238067u, 1994.*

Xu et al, Chemical Abstracts, vol. 106, No. 30035q, 1987.*

Barakat et ak, Chemical Abstracts, vol. 107, No. 93521m, 1987.*

Kenji Kobata et al., "Lipase–catalyzed synthesis of capsaicin analogs using natural oils as an acyl donor", *Biotechnology Letters,* vol. 20, No. 8, pp. 781–783, Aug. 1998.

H. Stamatis et al., "Studies on the Enzymatic Synthesis of Lipophilic Derivatives of Natural Antioxidants", *JAOCS,* vol. 76, No. 12, 1999.

B. Guyot et al., "Esterification of phenolic acids from green coffee with an immobilized lipase from Candida antarctica in solvent–free medium" *Biotechnology Letters,* vol. 19, No. 6, 1997.

J.W. Veldsink et al., "(Bio)synthesis and Application of New Antioxidants", $90^{th}$ AOCS Annual Meeting & Expo, Orlando, Florida, May 9–12, 1999.

* cited by examiner

*Primary Examiner*—James H Reamer
(74) *Attorney, Agent, or Firm*—M. Howard Silverstein; Curtis P. Ribando; John D. Fado

(57) ABSTRACT

Lipase-catalyzed transesterification reactions yield novel ferulyl-substituted or coumaryl-substituted acylglycerols with properties suitable for use as sunscreen agents having broad spectrum UV protection. These agents have the advantage of being synthesized from natural materials, while providing a value-added use for vegetable oils. They are readily incorporated into standard sunscreen formulations.

22 Claims, 1 Drawing Sheet

SUNSCREENS FROM VEGETABLE OIL AND PLANT PHENOLS

BACKGROUND OF THE INVENTION

1. Field of the Invention

This invention relates to ferulyl-substituted and coumaryl-substituted acylglycerols, their method of preparation through the transesterification of a triglyceride and a ferulic or coumaric ester, and the use of these compounds as sunscreen ingredients.

2. Description of the Prior Art

Health hazards associated with exposure to the sun are well established. The short term effect of excessive exposure to sunlight is erythema, commonly referred to as sunburn. Sunburn is primarily the result of UVB radiation having a wavelength of from about 290 nm to about 320 nm. Long term effects of exposure to sunlight include skin cancer (melanoma) and premature aging of the skin (including wrinkling, loss of elasticity, and pigment changes). These effects are predominantly caused by UVA radiation having a wavelength of from about 320 nm to about 400 nm. Public awareness of the dangers of sun exposure has stimulated the market for personal care products containing sunscreens.

Sunscreens function either as ultraviolet (UV) filters or UV blocks. UV blocks, such as $TiO_2$ and $ZnO$, as well as derivatives of other metal-oxides, form a physical barrier that scatters UV light (Fairhurst et al., "Particulate Sun Blocks: General Principles", Sunscreens: *Development, Evaluation, and Regulatory Aspects* $2^{nd}$ Edn, pp. 313–352, 1997). These UV blocks offer the most comprehensive sunscreen protection, blocking the full spectrum of UVA (400–320 nm) and UVB (320–290 nm) light. As a result of the particulate nature of these formulations, they often leave a noticeable residue when applied to the skin, which is cosmetically unacceptable to the consumer. The most commonly used sunscreens are UV filters, which are typically organic compounds incorporated at levels of about 2–15% into topical formulations (N. A. Shaath, "Evolution of Modern Sunscreen Chemicals", *Ibid*, pp. 3–33, 1997), (N. A. Shaath, "Quality Control of Sunscreens", *Ibid*, pp. 657–676, 1997). A disadvantage of UV filters is that each organic compound has a limited range of maximum UV absorptivity, rendering each reagent better suited for either UVA protection or UVB protection but not both. The advantage of the UV filtering molecules, however, is that they can be engineered to provide sunscreens with desirable physical appearance, solubility, and water resistant properties (N. A. Shaath, "Quality Control of Sunscreens", *Ibid*, pp. 657–676, 1997).

Although no longer used today, benzyl cinnamate formulated as an emulsion with benzyl salicylate, was used as a sunscreen as early as 1928 (N. A. Shaath, "Evolution of Modern Sunscreen Chemicals", *Ibid*, pp. 3–33, 1997). Today, cinnamic acid derivatives are the most widely used UVB absorbing chemicals in sunscreen formulations, with four derivatives approved for use in the United States and 17 approved for use in Europe (N. A. Shaath, "Evolution of Modern Sunscreen Chemicals", *Ibid*, pp. 3–33, 1997). The unsaturated C=C bond adjacent to the aromatic ring in cinnamates allows for a continuous, conjugated p-system throughout the molecule. An electron can be delocalized throughout the p-system by photo-excitation with energy corresponding to ~305 nm. Most common cinnamic acids and short chain esters are water soluble, limiting their usefulness as waterproof sunscreens. Cinnamic acid derivatives, therefore, have been designed with long chain hydrocarbons (i.e. octyl-p-methoxy cinnamate), which renders them water-insoluble and suitable for waterproof sunscreens. The $—OCH_3$ group of octyl-p-methoxy cinnamate acts as an electron-releasing group to improve the electron excitation process (N. A. Shaath, "Evolution of Modern Sunscreen Chemicals", *Ibid*, pp. 3–33, 1997).

There is currently a growing interest in modifying fats and oils to form structured lipids with specific properties for nutritional and pharmaceutical applications. Recent reviews have outlined the strategies for synthesizing tailor-made fats and oils and their desired properties (Willis et al., "Lipid Modification Strategies in the Production of Nutritionally Functional Fats and Oils", *Crit. Rev. Food Sci. Nutr.* 38:639–674, 1998), (F. D. Gunstone, "Movements Towards Tailor-Made Fats", *Prog. Lipid. Res.* 37:277–305, 1998). These strategies have included blending, distillation, fractionation, hydrogenation, interesterification with chemical catalysts, and more recently interesterification with biocatalysts. Chemical interesterifications of triacylglycerols for industrial applications are typically performed using inorganic catalysts at elevated temperatures (200–250° C.) (N. N. Gandhi, "Applications of Lipase", *J. Am. Oil Chem. Soc.* 74:621–633, 1997). Enzymatic interesterifications, however, offer the advantages of milder reaction conditions, a wider variety of synthetic substrates, and regioselective specificity towards the acyl groups of the triglycerols (Schmid et al., "Lipases: Interfacial Enzymes with attractive Applications", *Angew. Chem. Int. Ed.* 37:1608–1633, 1998).

SUMMARY OF THE INVENTION

We have now discovered lipase-catalyzed reactions are useful for synthesizing ferulyl-substituted or coumaryl-substituted acylglycerols with properties suitable for use as possible sunscreen agents. These agents are readily produced in high yield by means of transesterification of a triglyceride and a ferulic or coumaric ester.

The compounds of this invention are generally characterized by Formula I:

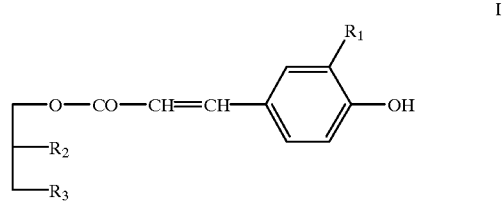

I wherein $R_1=OCH_3$ or H; and wherein $R_2$ and $R_3$ are each independently selected from OH and a C2–C24 fatty acid moiety.

In accordance with this discovery, it is an object of this invention to provide novel ferulyl-substituted or coumaryl-substituted acylglycerols having utility as sunscreen agents.

It is a further object of this invention to provide a facile and efficacious method of producing the subject sunscreen agents by means of a transesterification reaction.

It is also an object of the invention to produce a sunscreen agent that provides broad spectrum UV (UVA and UVB) protection.

Another object of the invention is to incorporate the ferulyl-substituted or coumaryl-substituted acylglycerols of the invention into sunscreen formulations.

A further object of the invention is to produce sunscreen agents that have the advantage of being synthesized from natural materials, while providing a value-added use for vegetable oils.

Other objects and advantages of this invention will become readily apparent from the ensuing description.

DETAILED DESCRIPTION

Figure 1:
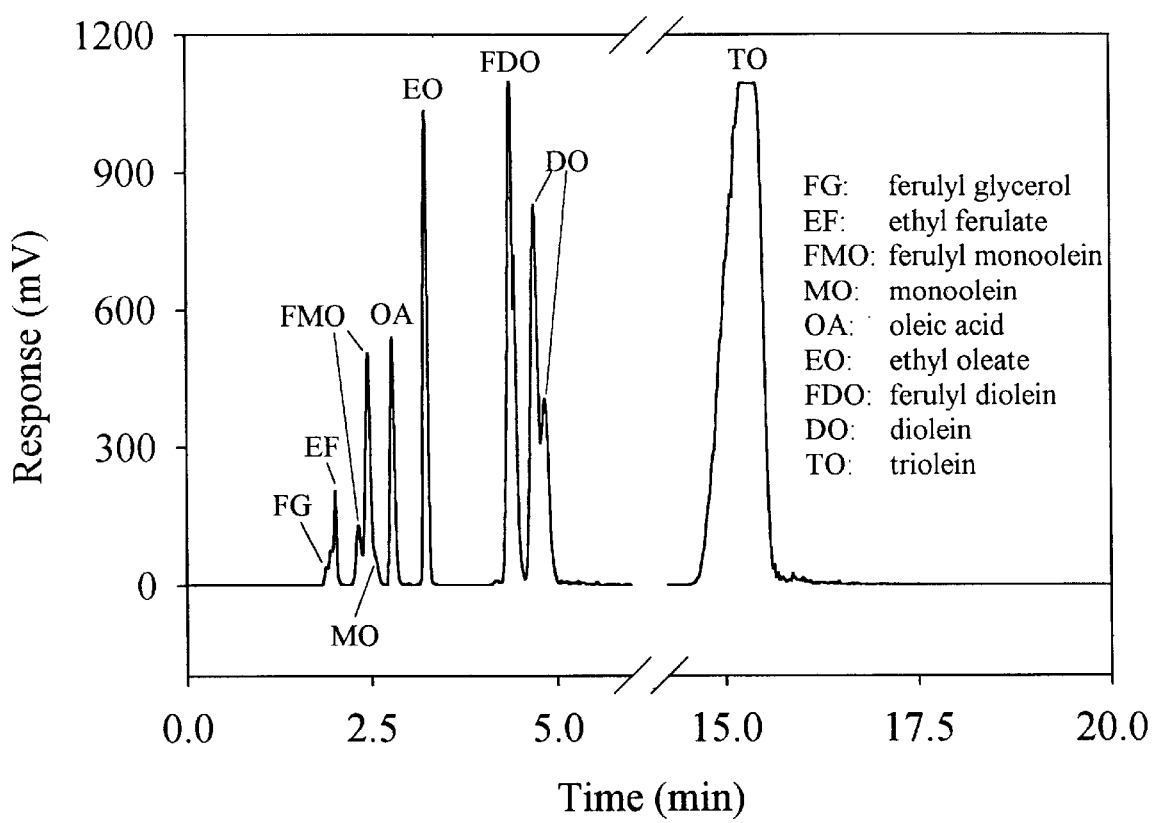
FIG. 1 is an HPLC analysis of the Novozym® 435 lipase-catalyzed transesterification of ethyl ferulate in neat triolein after 144 hours.

The substituted acylglycerols of the invention consist of a glycerol backbone in which one of the terminal hydroxyls is substituted with either a ferulate or a coumarate moiety, and at least one of the other two hydroxyls is substituted with a C2–C24 saturated or unsaturated fatty acid moiety. The natural isomers of plant phenols are trans. However, it is envisioned that the ferulate or coumarate moiety could also be cis. The 2-carbon of the glycerol backbone appears to be sterically hindered from esterifying with either of the phenolic acids. Sunscreen agents contemplated by Formula I include both substituted mono-acylglycerols wherein $R_2$ is OH and $R_3$ is a fatty acid moiety, as well as di-acylglycerols wherein both $R_2$ and $R_3$ are fatty acid moieties.

The sunscreen compounds of the invention are most readily produced in a lipase-catalyzed transesterification reaction between a glyceride and a simple acyl ester of ferulic or coumaric acid. C1–C10 acyl esters, and particularly C2–C8 acyl esters would be advantageously used in the transesterification reaction.

Preferably the glyceride is a triglyceride, particularly a natural vegetable oil. Exemplary oils include soybean oil, corn oil, sunflower seed oil, high-oleic sunflower seed oil, canola oil, safflower oil, cuphea oil, jojoba oil, coconut oil, palm kernel oil, and the like. These oils may have fatty acid moieties ranging in length from C2–C24, and having varying degrees of saturation from completely saturated to tri-unsaturated. Hydroxyl-substituted oils, such as ricinoleic, are also contemplated. When the products of the invention are intended for use in cosmetic formulations, it is preferred to select vegetable oils that are aromatically pleasing, particularly those having a relatively low level of linolenic acid, for example. Of course, synthetic triglycerides, such as triolein, could also be used as the starting material.

The preferred lipase for use herein is one having regioselective specificity towards the terminal acyl groups of a triglyceride. One such lipase is produced by *Candida antarctica*. This enzyme on an inert support is produced by Novo Nordisk (Franklinton, N.C., USA) under the tradename Novozym® 435.

The transesterification (glycerolysis) reaction is optimally conducted in the absence of oxygen, such as in vacuo or under nitrogen. The reaction may be carried out in a solventless system, or alternatively, using toluene or other suitable solvent for both the glyceride and the ferulate or coumarate ester reactants and also for the lipase catalyst. Temperature conditions for the reaction may range from about 20° C. to about 65° C., with the preferred temperatures being in the range of about 55° C. to about 60° C. In laboratory experiments with ethyl ferulate and with triolein as the triglyceride in an ethanol solvent, the reaction attains equilibrium in approximately 72 hours. In a solventless system with triolein, equilibrium is reached in about 144 hours. With or without solvent the combined yield of ferulyl monoolein and ferulyl diolein is in the range of about 70–80%.

Scheme 1, below, illustrates the transesterification process contemplated by the invention by showing the steps involved in the glycerolysis of ethyl ferulate with triolein to produce ferulyl-oleins. The left side of Scheme 1 illustrates involvement of the Novozym® 435 lipase in the removal of oleate groups from the triolein to form monoolein and diolein (A1). On the right side of Scheme 1, the lipase forms a cyclic, four heteroatom intermediate with the ethyl ferulate (A2). This complex dissociates to give the ferulyl-enzyme intermediate and ethanol as a byproduct (B2). The ferulyl-enzyme intermediate then interacts with the hydroxyl of a monoolein or diolein molecule (C2), which was formed by the parallel reaction (A1). In the final step (D2), the ferulyl-enzyme intermediate gives way to the ferulyl monoolein and the ferulyl diolein.

Scheme 1

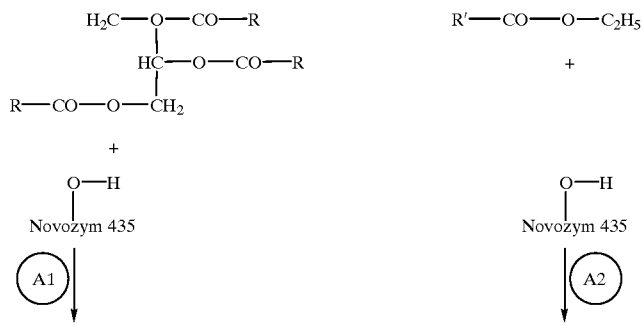

-continued

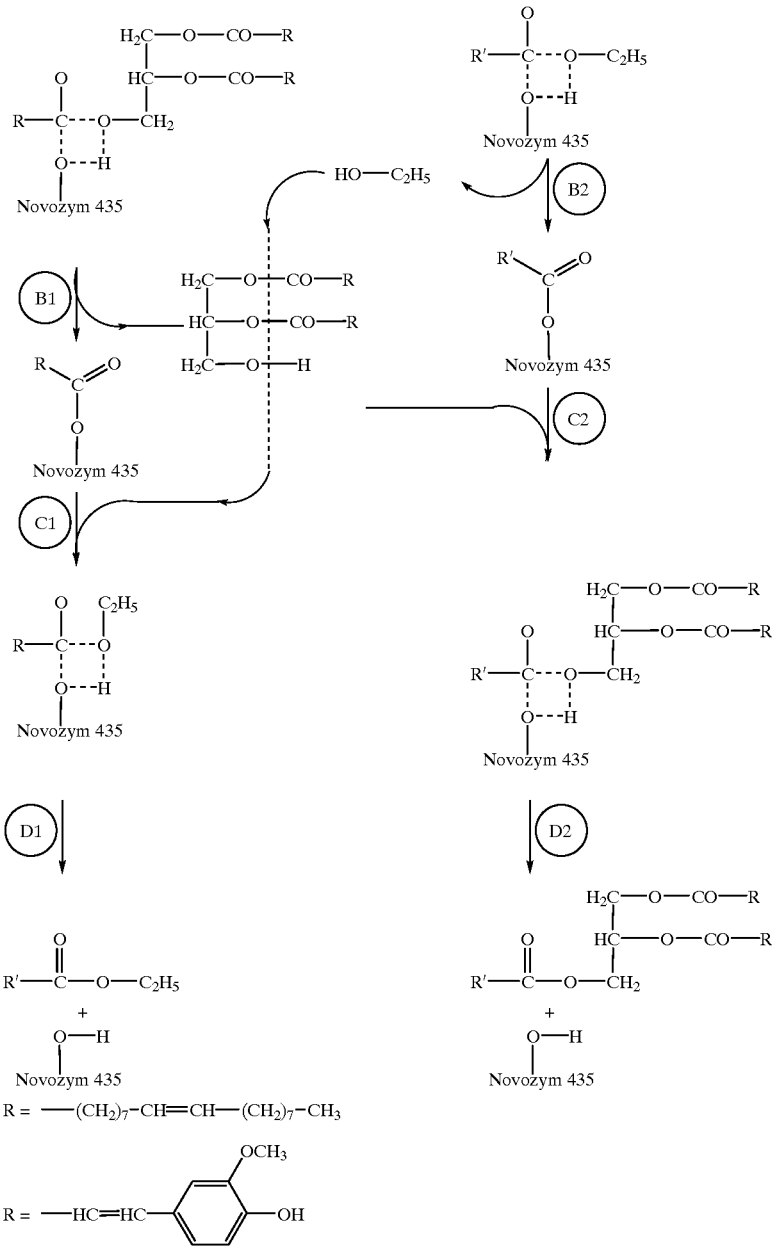

The ferulyl-substituted triacylglycerols of this invention are characterized by the properties of having the UV absorptivity of a cinnamate ester and the water-insoluble properties of a lipid, thereby rendering them useful as sunscreen agents for the skin that do not readily wash off with water. The UV absorbance of these products extends from about 280 nm to about 350 nm, and is particularly effective in the range of about 310–350 nm. This is predominantly in the UVA range, but also covers part of the UVB range. For additional UVB protection, the subject compounds may be formulated with other sunscreen agents as discussed, below.

The sunscreen agents of the invention as defined by the general formula (I) may be formulated into any cosmetic preparations that are especially designed to be water-resistant. The total level of sunscreen agent in these preparations will typically be on the order of about 0.1 to 20%, by weight, and preferably within the range of about 1–10%, by weight. The amount of sunscreen agent currently approved in the United States for inclusion in a topical skin treatment formulation is 15%. It is contemplated that the agents of this invention will be incorporated into formulations that are both effective and safe. An effective amount (or photoprotective amount) is that amount which is sufficient to significantly induce a positive effect of protection against UV sunlight as compared to a control. One measure of the effectiveness of the sunscreen agent is the Sun Protection Factor (SPF) of the composition. SPF is a commonly used measure of photoprotection of a sunscreen against sunburn. The SPF is defined as the ratio of the UV energy required to produce minimal erythema on protected skin to that required to produce the same minimal erythema on unprotected skin in the same individual. See Federal Register, 43, No. 166, pp. 38206–38269, Aug. 25, 1978). A safe amount is that which does not produce serious side effects.

The cosmetic preparation according to the invention can be formulated as a lotion, cream, gel, stick or aerosol. The base of the formulation may be a water-in-oil emulsion, an oil-in-water emulsion, an oil-in-oil alcohol lotion, a vesicular dispersion, or as an emulsifier-free starch/lipid dispersions as described in U.S. Pat. Nos. 5,676,994 and 5,882,713, both herein incorporated by reference. The term "oil" is used herein to be inclusive of all lipids. The term "lipid" (or fat) is a comprehensive term referring to substances which are found in living cells and which are comprised of only a nonpolar hydrocarbon moiety or a hydrocarbon moiety with polar functional groups (see the Encyclopedia of Chemistry, 3rd Edition, C. A. Hampel and G. G. Hawley, eds., 1973, p. 632, herein incorporated by reference). Most lipids are insoluble in water and are soluble in fat solvents such as ether and chloroform. Commonly used oils for cosmetic formulations include coconut oil, silicone oil and jojoba oil.

Other components that may be included in the sunscreen formulations of the invention include: other UVA and UVB sunscreen agents, such as 2-phenyl-benzimidazole-5-sulfonic acid, TEA salicylate, octyl dimethyl PABA, padimate-O (2-ethylhexyl 4-(dimethylamino) benzoate) and octyl methyl cinnamate.; inorganic physical sunblocks, such as zinc oxide and $TiO_2$; artificial tanning agents; abrasives; absorbents; fragrances; pigments; colorings/colorants; essential oils; skin sensates; astringents carriers and vehicles; thickening/structuring agents; emollients; emulsion stabilizers; excipients and auxiliaries commonly incorporated into cosmetic formulations; humectants; moisturizers; skin conditioners; anti-caking agents; antifoaming agents; antimicrobial agents; antioxidants; binders; buffering agents; bulking agents; chelating agents; chemical additives; film formers; humectants; opacifying agents; skin-conditioning agents; vitamins; and the like. Suitable emulsifiers include any of those conventionally used for cosmetic formulations, including for example, ethoxylated esters of natural derivatives, such as polyethoxylated esters of hydrogenated castor oil, a silicone oil emulsifier such as silicone polyol, free or ethoxylated fatty acid soap, an ethoxylated fatty alcohol, a free or ethoxylated sorbitan ester, an ethoxylated fatty acid or an ethoxylated glyceride. Exemplary agents and additives that could be included in formulations comprising the sunscreen agents of the invention, as well as suggested levels of addition, are given in U.S. Pat. No. 5,989,528 (Tanner et al.), which is herein incorporated by reference.

As previously indicated, the compositions of the invention are useful as sunscreen agents to provide protection from adverse effects of UV radiation. The principal application is as a topical sunburn protectant for human skin. However, it is envisioned that the compositions and formulations of the invention would also have veterinary applications as a skin protectant. The sunscreen formulations contemplated herein may be applied to the skin by spreading or spraying a thin layer thereof over the skin surface intended to be protected.

It is envisioned that the compounds of this invention may also have certain industrial applications, such as a UV protectant for epoxies, paints, and other consumer products. For these applications, the compounds could either be formulated into the material to be protected, such as by blending into a paint, or they could be applied as a separate coating.

The following examples are intended to further illustrate the invention, without any intent for the invention to be limited to the specific embodiments described therein.

EXAMPLE 1

Transesterification of Ethyl Ferulate with Triolein in Solvent.

Triolein (Nu-Chek-Prep® Elysian, Minn., 447 mg, 0.5 mmol) was dissolved in 5 mL of toluene in a 25 mL Schlenk tube at 60° C. Ethyl ferulate (ethyl 4-hydroxy-3-methoxy cinnamate, Sigma-Aldrich, 111 mg, 0.5 mmol) was added to the reaction mixture followed by Novozym® 435 lipase [*Candida antarctica*, with a 1–2% (w/w) water content, 110 mg, combined mass of the enzyme and its support]. Thus the ethyl ferulate and triolein reactants were present in a 1:1 mol ratio and were catalyzed by 1 wt equivalent (with respect to ethyl ferulate) of lipase. The reaction was performed under a nitrogen atmosphere using standard Schlenk line techniques. The suspension was stirred at 60° C., and 100 $\mu$L aliquots were periodically taken for analysis as described in Example 2, below. The reaction reached equilibrium after 72 h.

This reaction resulted in a 44% conversion of ethyl ferulate to the desired ferulyl monoolein and ferulyl diolein.

EXAMPLE 2

Transesterification of Ethyl Ferulate with Triolein without Solvent.

The procedure of Example 1 was repeated except the reaction was conducted in a solventless system. Ethyl ferulate (111 mg, 0.5 mmol) was dissolved in 1.24 g of triolein (1.4 mmol) at 60° C. to give a clear, colorless, and viscous solution. Additional triolein above the stoichiometric amount relative to the ethyl ferulate was needed to sufficiently suspend the lipase. Novozym® 435 lipase (110 mg) was added, and 20 $\mu$L aliquots were periodically taken for analysis by the HPLC and HPLC-APCI-MS, described above. The reaction reached equilibrium after 144 h. The longer time as compared to the reaction in toluene described in Example 1 is likely attributed to the higher viscosity of the neat triolein reaction and the resultant slower mass transfer of the ethyl ferulate. The combined yield of ferulyl monoolein and ferulyl diolein was 77%, representing a 33% increase over the yield obtained in Example 1.

High Performance Liquid Chromatography (HPLC) Analysis.

Analyses were performed using a Thermo Separation Products (San Jose, Calif.) HPLC system consisting of a Spectra System® AS3000 autosampler, a Spectra System® P4000 pump, a Spectra System® UV6000LP detector, an Alltech® (Deerfield, Ill.) 500 Evaporative Light-Scattering Detector (ELSD), and a Prodigy $C_8$ column (5 $\mu$m, 250×4.6 mm, Phenomenex®, Torrance, Calif.). Solvents were filtered using Whatman 0.45 $\mu$m nylon membrane filters (Sigma-Aldrich) and degassed using a Thermo Separation Products® SCM 1000 Membrane Degasser.

For determination of triolein and its derivatives, the 100 $\mu$L and 20 $\mu$L aliquots taken from the glycerolysis reactions were diluted to 1 mL with acetone and filtered through 0.45 mm Gelman Acrodisc® 13LC PVDF syringe filters. Injections of 10 $\mu$L were eluted from the column at a flow rate of 1.5 mL/min using an isocratic flow of 40/60 (v/v) acetone (containing 1% glacial acetic acid)/acetonitrile. The eluate was monitored at 360 nm using the Spectra System® UV6000LP detector followed by the Alltech® 500 ELSD (nitrogen; 2.0 slpm, 70° C.). The detectors were plumbed in series with a void volume resulting in a 0.1 s delay in peak retention time for species detected by both methods. It should be noted that the ELSD response is not linear and that peak intensities and areas are species dependent; therefore, the tabulated data are intended for qualitative comparisons only.

The chromatogram obtained from the HPLC analysis of the reaction shows nine peaks detected by ELSD. The peaks are illustrated in FIG. 1, which depicts the HPLC analysis of the transesterification performed in neat Triolein (discussed below). Table 1 lists the peak assignments, the corresponding retention times ($R_t$), and relative yields of the reaction products. The peaks corresponding to ethyl ferulate (EF), monoolein (MO), oleic acid (OA), ethyl oleate (EO), diolein (DO), and triolein (TO) were identified based on retention times determined from standards. This left four unidentified, UV-absorbing species with retention times of 1.8, 2.4, 2.5, and 4.4 min. These compounds were identified by HPLC-Atmospheric Pressure Chemical Ionization-Mass Spectroscopy (HPLC-APCI-MS) Analysis, as follows:

(HPLC-APCI-MS) Analysis.

HPLC-APCI-MS analyses were performed on samples prepared for HPLC analysis (see above). Elution conditions were identical to those described above except glycerolysis reaction samples were eluted using an isocratic flow of 40/60 (v/v) methanol (containing 1% glacial acetic acid)/acetonitrile. Mass spectral analyses were performed using a Finnigan (San Jose, Calif.) MAT LCQ mass spectrometer with a direct liquid APCI interface.

HPLC-APCI-MS was used to determine that the four reaction products with retention times of 1.8, 2.4, 2.5, and 4.4 min were monoolein or diolein derivatives containing ferulyl moieties. Scheme 1 shows the structures of the reactants and the UV-absorbing products of interest. The major ion corresponding to the peak at $R_t$=1.8 min was 251 m/z and is ferulyl glycerol (FG) with a major ion value of $[M+H-H_2O]^+$. An ion corresponding to diferulyl glycerol (427 m/z, $[M+H-H_2O]^+$) was not observed. The loss of $H_2O$ from a monoacylglycerol during HPLC-APCI-MS analysis was expected and has been previously documented (Neff et al., "Characterization of Model Triacylglcerol (Triolein, tilinolein, and trilinolenin) Autooxidation Products via High-Performance Liquid Chromatogrphy Coupled with Atmospheric Pressure Chemical Ionization Mass Spectroscopy", J. Chromatogr. A 818:169–186, 1998). Similarly, the peaks at $R_t$=2.4 and 2.5 min possessed major ions of 515 m/z $[M+H-H_2O]^+$ and were identified as isomers of ferulyl monoolein (FMQ). It is believed that the peaks at $R_t$=2.4 min and $R_t$=2.5 min are the result of at least two FMQ isomers, most likely being the 1-ferulyl-3-monoolein and 1-ferulyl-2-monoolein. The formation of a third isomer, 2-ferulyl-1-monoolein, is improbable due to the size of the ferulyl moiety and the steric restrictions of the sn-2 position of the lipid. The last UV-A species ($R_t$=4.4 min) formed from the glycerolysis corresponds to a major ion of 796 m/z, $[M]^+$, and was identified as ferulyl diolein (FDO). The presence of a single peak for FDO is consistent with the formation of a single isomer, most probably 1-ferulyl-2,3-diolein.

EXAMPLE 3

Transesterification of Ethyl Ferulate with Triolein without Solvent Using Recycled Lipase.

The catalytic stability of Novozym® 435 lipase was demonstrated by repeating the transesterification of ethyl ferulate and with neat TO with previously used lipase. After equilibrium was reached in the reaction described in Example 2, the triolein was decanted, and fresh triolein was added to the reaction vessel. Residual quantities of ethyl ferulate and reaction products from the reaction of Example 2 were determined by HPLC and subtracted from the yields obtained from the second reaction. Ethyl ferulate was added to initiate the reaction, which stirred for an additional 120 h. HPLC analysis revealed that the second glycerolysis produced 31% ferulyl monolein and 43% ferulyl diolein, a combined yield of 74%. The residual amounts of ethyl ferulate and ferulyl glycerol after 120 h were 17% and 9%, respectively. The slightly higher quantity of unreacted ethyl ferulate present at equilibrium (17%) compared to the quantity of unreacted ethyl ferulate present at equilibrium in the original glycerolysis (13%) is attributed to the shorter reaction time. These results indicate that Novozym® 435 lipase remains active at 60° C. for weeks and is able to catalyze multiple glycerolysis reactions.

EXAMPLE 4

Transesterification of Ethyl Ferulate with Vegetable Oil

Using standard Schlenk line techniques, 44.4 g (0.20 mol) of ethyl ferulate (Sigma-Aldrich®) was dissolved in 500 mL (0.52 mol) of vegetable oil (Crisco® Brand) while stirring at 60° C. under a nitrogen atmosphere. 34.0 g of Novozym® 435 lipase was added and the slurry was stirred for 115 h. The slurry was separated by filtration through Whatman® 54 (12.5 cm) filter paper. HPLC analysis of the product was conducted as described in Example 2.

The reaction (with a 2.6:1 mole ratio of vegetable to ethyl ferulate) resulted in a 80% yield (based on the total peak area of the UV-absorbing species) of the sunscreen active ingredients, ferulyl monoacylglycerols and ferulyl diacylglycerols. This corresponds to 24% (w/w) of active ingredient in the final 500 mL of flitrate.

EXAMPLE 5

The sun protection factor (SPF) of a 15% (w/w) solution of the sunscreen product prepared in Example 4 in soybean oil was determined by a standard in vitro method to be 10.2. When small amounts of stabilizing compounds, octyl methoxycinnamate and HallBrite TQ® (C.P. Hall CO.) were added, the photostability of the 15% solution showed a loss of 2 SPF after a succession of increasing UV doses over an hour.

TABLE 1

Peak Assignments and Relative Yields for the Alcoholysis and Transesterification Products of Ethyl Ferulate

| | | | relative peak areas[a] | | |
|---|---|---|---|---|---|
| $R_t$ (m) | peak | major ion (m/z)[b] | MO[c] | TO[c] | TO (neat)[d] |
| 1.8 | FG | 251 | 2.6(44%)[e] | 0.4(19%) | —(10%) |
| 2.0 | EF | — | 1.0(32%) | 1.0(37%) | 1.0(13%) |
| 2.4, 2.5 | FMO | 515 | 2.4(24%) | 1.3(32%) | 3.6(29%) |
| 2.6 | MO | — | 2.2 | — | — |
| 2.8 | OA | — | — | 0.2 | 2.5 |
| 3.2 | EO | — | 0.4 | 1.3 | 4.6 |
| 4.4 | FDO | 796 | —(0%) | 0.6(12%) | 8.1(48%) |
| 4.7, 4.9 | DO | — | 1.0 | 1.2 | 9.0 |
| 15.2 | TO | — | — | 4.1 | 40.2 |

[a]Peaks were obtained using the ELSD, and the areas are relative for each reaction based on EF.
[b]The major ions detected by HPLC-APCI-MS were identified as follows: FG, $[M + H - H_2O]^+$; FMO, $[M + H - H_2O]^+$; FDO, $[M]^+$.
[c]Alcoholysis and transesterification of 0.1M EF with 0.1M MO and TO in 5 mL toluene catalyzed by 110 mg of Novozym ® 435 lipase for 72 h.
[d]Transesterification of 0.36M EF in 1.4 mL TO catalyzed by 110 mg of Novozym ® 435 lipase for 144 h.
[e]Percent yields for the UV-A species produced in each reaction were calculated based on the total peak area recorded using the UV6000LP detector.

We claim:

1. A compound having the structural formula:

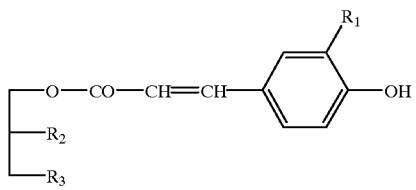

wherein $R_1$=H or $OCH_3$; and
wherein one of $R_2$ or $R_3$ is a C2–C24 fatty acid moiety and the other of $R_2$ or $R_3$ is either a C2–C24 fatty acid moiety or OH.

2. The compound of claim 1, wherein $R_1$ is $OCH_3$.

3. The compound of claim 1, wherein one of $R_2$ or $R_3$ is OH.

4. The compound of claim 1, wherein both $R_2$ and $R_3$ are C2–C24 fatty acid moieties.

5. The compound of claim 1, wherein $R_1$ is $OCH_3$ and wherein one of $R_2$ or $R_3$ is a C18 fatty acid moiety and the other of $R_2$ or $R_3$ is OH.

6. The compound of claim 5, wherein the C18 fatty acid moiety is a monoene.

7. The compound of claim 1, wherein $R_1$ is $OCH_3$ and wherein both $R_2$ and $R_3$ are C18 fatty acid moieties.

8. The compound of claim 7, wherein at least one of the C18 fatty acid moieties is a monoene.

9. A sunscreen formulation comprising:
(1) a sunscreen agent having the structural formula:

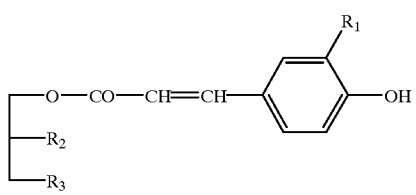

wherein $R_1$=H or $OCH_3$; and
wherein one of $R_2$ or $R_3$ is a C2–C24 fatty acid moiety and the other of $R_2$ or $R_3$ is either a C2–C24 fatty acid moiety or OH; and
(2) a carrier for the sunscreen agent;
wherein said agent is present in said formulation at a level in the range of about 0.1 to 20% by weight.

10. The formulation of claim 9, wherein said agent is present in the range of about 1–10% by weight.

11. The formulation of claim 9, wherein said wherein $R_1$ is $OCH_3$.

12. The formulation of claim 9, wherein $R_1$ is $OCH_3$ and wherein at least one of $R_2$ and $R_3$ is a C16 or C18 fatty acid moiety.

13. The compound of claim 12, wherein said C16 or C18 fatty acid moiety is an unsaturated.

14. A method of making a compound having the structural formula:

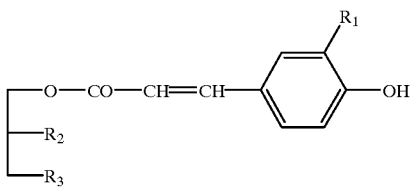

wherein $R_1$=H or $OCH_3$; and
wherein one of $R_2$ or $R_3$ is a C2–C24 fatty acid moiety and the other of $R_2$ or $R_3$ is either a C2–C24 fatty acid moiety or OH;
comprising the steps:
 a. reacting in a reaction mixture an ester of ferulic or coumaric acid with a triglyceride in the presence of a lipase catalyst under conditions that permit transesterification of said ester and said triglyceride; and
 b. recovering said compound from said reaction mixture.

15. The method of claim 14, wherein said reaction mixture comprises a solvent other than said triglyceride.

16. The method of claim 14, wherein said reaction mixture does not comprise a solvent other than said triglyceride.

17. The method of claim 14, wherein said ester is ethyl ferulate.

18. The method of claim 14, wherein said triglyceride is a vegetable oil.

19. The method of claim 14, wherein said triglyceride is a vegetable oil selected from the group consisting of soybean oil, corn oil, sunflower seed oil, high-oleic sunflower seed oil, canola oil, safflower oil, cuphea oil, jojoba oil, coconut oil, and palm kernel oil.

20. A product produced by the process of claim 14.

21. A product produced by the process of claim 17.

22. A product produced by the process of claim 18.

* * * * *